(12) United States Patent
Yamamoto et al.

(10) Patent No.: US 7,598,425 B2
(45) Date of Patent: Oct. 6, 2009

(54) METHOD FOR PRODUCING HYDRATE OF FLUOROALKYL KETONE

(75) Inventors: Yoshihiro Yamamoto, Settsu (JP); Yoshichika Kuroki, Settsu (JP); Daisuke Karube, Settsu (JP); Tatsuya Ohtsuka, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 51 days.

(21) Appl. No.: 11/578,523

(22) PCT Filed: Apr. 8, 2005

(86) PCT No.: PCT/JP2005/006905

§ 371 (c)(1),
(2), (4) Date: Jul. 20, 2007

(87) PCT Pub. No.: WO2005/102972

PCT Pub. Date: Nov. 3, 2005

(65) Prior Publication Data

US 2008/0262273 A1   Oct. 23, 2008

(30) Foreign Application Priority Data

Apr. 19, 2004   (JP) ............................. 2004-123045

(51) Int. Cl.
*C07C 29/48* (2006.01)
(52) U.S. Cl. .................. 568/846; 568/842; 568/844
(58) Field of Classification Search .................. 568/846, 568/842, 844
See application file for complete search history.

(56) References Cited

U.S. PATENT DOCUMENTS

| 3,321,515 | A | 5/1967 | Moore | 260/544 |
|---|---|---|---|---|
| 4,334,099 | A | 6/1982 | Van De Puy | 568/386 |
| 4,337,361 | A | 6/1982 | Anello | 568/386 |
| 4,734,169 | A | 3/1988 | Yokoi et al. | 204/79 |
| 5,498,799 | A | 3/1996 | Torihara et al. | |

FOREIGN PATENT DOCUMENTS

| JP | 40-27173 | | 11/1958 |
|---|---|---|---|
| JP | 53-25521 | | 3/1978 |
| JP | 57-158736 | | 9/1982 |
| JP | 57-203026 | | 12/1982 |
| JP | 58-62130 | | 4/1983 |
| JP | 61-277645 | | 12/1986 |
| JP | 63-35537 | | 2/1988 |
| JP | 63035537 | * | 2/1988 |
| JP | 64-26527 | | 1/1989 |
| JP | 01-203339 | | 8/1989 |
| JP | 7-69959 | | 3/1995 |
| JP | 8-231448 | | 9/1996 |
| JP | 09-509425 | | 9/1997 |
| JP | 2001-81056 | | 3/2001 |
| WO | WO 95/23124 | | 8/1995 |
| WO | WO 03/008366 | | 1/2003 |

OTHER PUBLICATIONS

V. Grakauskas; "Aqueous Fluorination of Carboxylic Acid Salts;" J. Organic Chemistry, 34 (Feb. 19, 1969) p. 2446.
Beilstein Data XP-00247050, 1974.
Supplementary European Search Report dated Feb. 28, 2008.

* cited by examiner

*Primary Examiner*—Elvis O Price
(74) *Attorney, Agent, or Firm*—Wenderoth, Lind & Ponack, L.L.P.

(57) ABSTRACT

The present invention relates to a method for producing a compound represented by formula (2):

$$[CF_3(CF_2)_n][CF_3(CF_2)_m]C(OH)_2 \qquad (2)$$

wherein n and m independently represent 0 to 10, the method comprising reacting with a halogen or a halogen-containing oxidizing agent a salt of a compound represented by formula (1):

$$[CF_3(CF_2)_n][CF_3(CF_2)_m]C(OH)COOH \qquad (1)$$

wherein n and m independently represent 0 to 10.

40 Claims, No Drawings

METHOD FOR PRODUCING HYDRATE OF FLUOROALKYL KETONE

TECHNICAL FIELD

The present invention relates to a method for producing hydrates of fluoroalkyl ketones, in particular, of hexafluoroacetone (which may hereafter be abbreviated to "HFA").

More particularly, the invention relates to a method for producing a HFA hydrate for the purpose of making effective use of a 3,3,3-trifluoro-2-trifluoromethyl-2-hydroxypropionic acid.

HFA hydrates are useful as synthetic intermediates for a variety of fluorine compounds. For example, HFA is reacted with a variety of aromatic compounds for use as a crosslinking agent for rubber, monomer for fluorine-containing polyimides, etc.

HFA hydrates are also reduced to hexafluoroisopropanol by hydrogen reduction for use as starting materials for anesthetics.

BACKGROUND ART

Heretofore, various HFA production methods are known and for example, Patent Documents 1 to 4 propose methods for isomerizing hexafluoropropylene oxide. Hexafluoropropylene oxide is known to be obtained by a method of oxidizing hexafluoropropene with oxygen, which is disadvantageous in that the oxidation yield is low and production cost is high.

In addition to this method, a method for oxidizing hexafluorothioacetone dimer is known (Patent Documents 5 to 8, etc.), which is disadvantageous in that the yield is low and purification is difficult. Moreover, a method for fluorinating hexachloroacetone by HF is known, which poses a problem in that purification is not easy (Patent Document 9).

In view of the above-described problems, attempts have been made to produce hexafluoroacetone using, as a starting material, a derivative of octafluoroisobutene, which is a by-product produced when hexafluoropropene is produced. For example, Patent Document 10 discloses a method for oxidizing octafluoroisobutyl methyl ether with oxygen in the presence of an activated carbon catalyst. However, the inventors of the present invention found by testing this method that hexafluoroacetone was temporarily obtained but the catalyst activity of activated carbon was noticeably degraded, and thus this method was not technically carried out. In addition, Patent Documents 11 to 14 disclose methods for producing hexafluoroacetone from a derivative of octafluoroisobutyl methyl ether, but all of the methods have a low yield, and none of them are suitable as a method for producing industrially hexafluoroacetone at low cost.

Non-patent Document 1 discloses decarboxylation of a salt of carboxylic acids by reacting it with fluorine gas in an aqueous solution. Such decarboxylation, however, does not proceed with chlorine gas.

[Patent Document 1] U.S. Pat. No. 3,321,515

[Patent Document 2] Japanese Unexamined Patent Publication No. 1978-25512

[Patent Document 3] Japanese Unexamined Patent Publication No. 1983-62130

[Patent Document 4] WO 03/008366

[Patent Document 5] U.S. Pat. No. 4,337,361

[Patent Document 6] U.S. Pat. No. 4,334,099

[Patent Document 7] Japanese Unexamined Patent Publication No. 1982-158736

[Patent Document 8] Japanese Unexamined Patent Publication No. 1982-203026

[Patent Document 9] Japanese Examined Patent Publication No. 1965-27173

[Patent Document 10] Japanese Unexamined Patent Publication No. 1989-203339

[Patent Document 11] Japanese Unexamined Patent Publication No. 1986-277645

[Patent Document 12] Japanese Unexamined Patent Publication No. 1989-26527

[Patent Document 13] Published Japanese Translation of PCT International Publication for Patent Application No. 1997-509425

[Patent Document 14] Japanese unexamined Patent Publication No. 2001-81056

[Non-patent Document 1] J. Org. Chem. 34, 2446 (1969)

DISCLOSURE OF THE INVENTION

Problem to be Solved by the Invention

An object of the invention is to readily produce hydrates of fluoroalkyl ketones in high yields.

Means for Solving the Problem

The inventors of the present invention found that the reaction of a fluoroalkyl hydroxycarboxylic acid salt with a halogen or a halogen-containing oxidizing agent yields the corresponding ketone hydrate.

The invention relates to a method as summarized below.

1. A method for producing a compound represented by formula (2): $[CF_3(CF_2)_n][CF_3(CF_2)_m]C(OH)_2$ (2) wherein n and m independently represent 0 to 10, the method comprising reacting with a halogen or a halogen-containing oxidizing agent a salt of a compound represented by formula (1): $[CF_3(CF_2)_n][CF_3(CF_2)_m]C(OH)COOH$ (1) wherein n and m independently represent 0 to 10.

2. The method according to item 1, wherein the salt of the compound represented by formula (1) is a 3,3,3-trifluoro-2-trifluoromethyl-2-hydroxypropionic acid, wherein n=m=0.

3. The method according to item 1 or 2, wherein the halogen or halogen-containing oxidizing agent is fluorine diluted with an inert gas.

4. The method according to item 1 or 2, wherein the halogen or halogen-containing oxidizing agent is chlorine.

5. The method according to item 1 or 2, wherein the halogen or halogen-containing oxidizing agent is a hypochlorite or a hypobromite.

6. The method according to any one of items 1 to 5, wherein water is used as a solvent for reacting the salt of the compound of formula (1) with the halogen or halogen-containing oxidizing agent.

7. The method according to any one of items 1 to 6, wherein the salt of the compound of formula (1) is a Li salt, K salt or Na salt.

8. The method according to any one of items 1 to 6, wherein a solvent having a pH of 4 or more is used for reacting the salt of the compound of formula (1) with the halogen or halogen-containing oxidizing agent.

9. The method according to any one of items 1 to 8, wherein chlorine or bromine is produced in the reaction system.

Effects of the Invention

In accordance with the invention, compounds represented by formula (2): $[CF_3(CF_2)_n][CF_3(CF_2)_m]C(OH)_2$ (2) wherein n and m independently represent 0 to 10 can be obtained in high yields using salts of compounds represented by formula (1): $[CF_3(CF_2)_n][CF_3(CF_2)_m]C(OH)COOH$ (1) wherein n and m independently represent 0 to 10.

In particular, the useful materials HFA hydrates can be obtained in high yields, using 3,3,3-trifluoro-2-trifluoromethyl-2-hydroxypropionic acids which can be easily synthesized from industrial wastes.

BEST MODE FOR CARRYING OUT THE INVENTION

While not desiring to be bound in any way by theory, the inventors believe that the reaction of the invention proceeds by hydrolysis of a halogenated compound resulting from decarboxylative halogenation reaction, as illustrated in the example of the reaction scheme of a HFA hydrate shown below:

[Reaction Scheme 1]

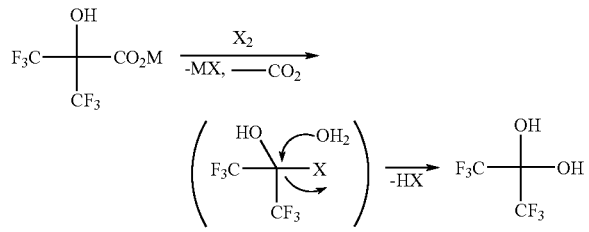

wherein X is a halogen atom; and M is a monovalent ($M^+$), bivalent ($\frac{1}{2}M^{2+}$) or trivalent ($\frac{1}{3}M^{3+}$) ion. Preferably, $M^+$ is a monovalent cation such as $Li^+$, $K^+$, $Na^+$, $NH_4^+$, $Ag^+$ or the like; a bivalent cation such as $\frac{1}{2}Mg^{2+}$, $\frac{1}{2}Ca^{2+}$, $\frac{1}{2}Sr^{2+}$, $\frac{1}{2}Ba^{2+}$, $\frac{1}{2}Pb^{2+}$, $\frac{1}{2}Cu^{2+}$ or the like; or a trivalent cation such as $\frac{1}{3}Al^{3+}$ or the like.

J. Org. Chem. 34, 2446 (1969) reported that a salt of carboxylic acids reacts with fluorine gas in aqueous solutions to undergo decarboxylative halogenation reaction, but such reactions do not proceed with chlorine and bromine, because the intermediate perhalides (—COOX) hydrolyze to form carboxylic acids.

Surprisingly, it was found that according to the method of the invention, such reactions easily proceed not only with fluorine but also with chlorine and bromine, although it is not clear whether the aforementioned intermediates are formed during such reactions.

The inventors conducted a detailed examination of halogenation conditions, and found that a hexafluoroacetone hydrate can be produced by reacting a carboxylic acid compound of formula (1) not only with a halogen but also with a hypochlorite or hypobromite as a halogen-containing oxidizing agent. It is likely that hypochlorites, which can liberate chlorine in acidic conditions, are releasing chlorine during the reaction system, but the reaction of the invention proceeds similarly with an alkali; hence, the mechanism by which the reaction with a hypochlorite proceeds is not clear.

Salts of compounds of formula (1) are represented by formula (1A) shown below. Such salts include known substances disclosed in Japanese Unexamined Patent Publication No. 2002-234860, or are readily obtainable from known salts or corresponding carboxylic acid compounds via salt exchange reactions or salt formation reactions.

Formula (1A):

$$[CF_3(CF_2)_n][CF_3(CF_2)_m]C(OH)COO^-M^+ \quad (1A)$$

wherein n and m independently represent 0 to 10; and M is a monovalent ($M^+$), bivalent ($\frac{1}{2}M^{2+}$) or trivalent ($\frac{1}{3}M^{3+}$) ion. Preferably, $M^+$ is a monovalent cation such as $Li^+$, $K^+$, $Na^+$, $NH_4^+$, $Ag^+$ or the like; a bivalent cation such as $\frac{1}{2}Mg^{2+}$, $\frac{1}{2}Ca^{2+}$, $\frac{1}{2}Sr^{2+}$, $\frac{1}{2}Ba^{2+}$, $\frac{1}{2}Pb^{2+}$, $\frac{1}{2}Cu^{2+}$ or the like; or a trivalent cation such as $\frac{1}{3}Al^{3+}$ or the like.

Salts other than those specifically mentioned above are readily obtainable from compounds of formula (1) or salts of formula (1A) in accordance with conventional processes.

Among the compounds represented by the aforementioned formula (2), HFA hydrates where n and m are both 0 are especially useful. A method for producing the starting material, a 3,3,3-trifluoro-2-trifluoromethyl-2-hydroxypropionic acid ester, is known as disclosed in, for example, Japanese Unexamined Patent Publications No. 1986-286348 and No. 2002-234860. This method comprises reacting octafluoroisobutene with methanol to give octafluoroisobutyl methyl ether; and reacting the octafluoroisobutyl methyl ether with an alkali metal hydroxide to extract hydrogen fluoride therefrom, thereby producing heptafluoroisobutenyl methyl ether which is subjected to oxidization:

$(CF_3)_2C=CF_2+MeOH\rightarrow(CF_3)_2CHCF_2OMe\rightarrow(CF_3)_2C=CFOMe\rightarrow(CF_3)_2C(OH)-CO_2Me$ Examples of starting carboxylic acid salts produced by hydrolysis of the ester portion of the aforementioned 3,3,3-trifluoro-2-trifluoromethyl-2-hydroxypropionic acid esters include salts of Li, K, Na, Mg, Ca, Sr, Ba, Pb, Cu, Al, $NH_4$, Ag, etc. Among such examples, Li, K, Na, Ca and Mg salts are preferable as starting materials for use in the method of the invention; and Na and K salts are more preferable.

A carboxylic acid salt that has been purified by a conventional process such as solvent extraction can be used as the starting carboxylic acid salt, but a crude solution obtained by hydrolyzing a methyl ester with an alkali metal hydroxide such as KOH, NaOH or the like can also be used. An excess of alkali metal hydroxide promotes decomposition of a halogen during reaction with the halogen; therefore, it may be neutralized with an acid such as hydrochloric or sulfuric acid.

The carboxylic acid salt may also be prepared by using a carboxylic acid as the starting material, and forming a salt in the reaction solution.

Water is preferable as a solvent for carrying out the halogenation reaction of the invention; however, the solvent may also be an aqueous solution containing an organic solvent that may be used in synthesizing a carboxylic acid salt from a 3,3,3-trifluoro-2-trifluoromethyl-2-hydroxypropionic acid ester, such as, for example, methanol, ethanol, acetone, dioxane, tetrahydrofuran, acetonitrile, etc.

The reaction temperature is not limited so long as it is above the freezing point of the solvent, and is typically from about −20 to about 100° C., with a preferable range being from about −5 to about 50° C. When the reaction solvent is water, the reaction temperature is not limited so long as the water is not frozen by the depression of the freezing point. The reaction temperature may be cooled down to about −20° C., but is typically from about −5 to about 80° C., and preferably from about 0 to about 50° C. If the reaction temperature is high, undesired side reaction may occur, whereas if it is too low, there may be greater losses of halogen or halogen-containing oxidizing agent. When chlorine is used as a halogen or halogen-containing oxidizing agent, the reaction temperature is preferably from about 30 to about 50° C., although the optimal temperature depends upon the halogen or halogen-containing oxidizing agent.

The concentration of the starting material in the reaction solution is not limited, but a preferable concentration is from 5 to 60 mass %. The use of a dilute solution deteriorates the reaction efficiency of halogen, accompanied by greater losses of halogen; therefore, the reaction solution preferably has a high concentration. Even if halogen is added to a reaction solution from which a carboxylic acid salt has precipitated because of saturation, the reaction proceeds without any particular problems.

Suitable examples of halogens include, but are not limited to, fluorine, chlorine and bromine; and suitable examples of halogen-containing oxidizing agents include, but are not limited to, hypochlorites such as, for example, sodium hypochlorite, lithium hypochlorite, potassium hypochlorite and calcium hypochlorite, and hypobromites such as, for example, sodium hypobromite, lithium hypobromite, potassium hypobromite, and calcium hypobromite. Chlorine is especially suitable because it is inexpensive. Chlorine may be directly used as a purified gas or may be used for the reaction while being produced in the reaction system. Chlorine may be produced in the reaction system by, for example, adding an alkali metal chloride or an alkaline-earth metal chloride to the reaction system, and subsequently electrolyzing the chloride. Bromine can also be produced in the similar manner.

When $F_2$ gas is used as a halogen, it is preferably diluted with a gas inert to fluorine. The diluent gas may be selected from nitrogen, helium, air, hydrofluoroalkanes, perfluoroalkanes, perfluoroketones, etc., but nitrogen is most preferable in view of its low cost. The concentration of $F_2$ is from 1 to 30 mass %, and preferably from 4 to 20 mass %. If the concentration of $F_2$ is high, vigorous undesired side reactions such as combustion are liable to occur, which can be dangerous. Although dilute $F_2$ can be used without any particular problems, the diluent gas may increase accompanying losses of the target product such as a HFA hydrate.

The amount of halogen or halogen-containing oxidizing agent used for the reaction is not limited; but it is preferably from about 0.5 to about 10 molar equivalents, and more preferably from about 0.9 to about 2 molar equivalents. Increasing the equivalent of halogen used results in an improved conversion of the starting material.

The rate of addition of halogen or halogen-containing oxidizing agent is not limited; in general, it is preferably from about 0.5 to about 50 hours per equivalent of halogen, and more preferably from about 0.5 to about 10 hours.

When diluted $F_2$ gas is used, the flow rate of the gas may be from 0.1 to 5 times the volume of the reaction vessel per minute, and preferably from 0.5 to 2 times. If the flow rate is high, losses of $F_2$ gas become greater, whereas if the flow rate is low, the reaction time is lengthened, resulting in poor productivity. When chlorine gas is used, the flow rate of the gas may be from 0.01 to 5 times the volume of the reaction vessel per minute, and preferably from 0.1 to 1 times. When bromine is used, about 0.5 to about 10 molar equivalents of bromine (liquid) may be added to the reaction solution by, for example, dropping.

The reaction time is not limited, and is typically from about 0.5 to about 50 hours. The reaction of the invention can be carried out in batch mode, or carried out continuously by supplying the starting carboxylic acid solution and halogen to the reaction vessel, and simultaneously extracting the reaction solution.

The solution for carrying out the reaction of the invention, in particular an aqueous solution or water-containing solution, preferably has a pH of 3.0 to 13.0, and more preferably a pH of 4.0 to 11.0. If the pH is low, the reaction proceeds slowly, resulting in greater losses of halogen or halogen-containing oxidizing agent. In contrast, if the pH is too high, decomposition of a fluoroalkyl ketone hydrate (in particular, hexafluoroacetone hydrate) by alkali occurs. In order to prevent the pH from decreasing as the reaction proceeds, it is preferable to add alkaline compound(s), as necessary, before or during the reaction. Examples of preferable alkalis added include carbonates, hydrogencarbonates, sesquicarbonates, phosphates, hydroxides and the like of alkali metals and alkaline-earth metals. Carbonates and hydrogencarbonates are especially preferable for preventing decomposition of halogen and fluoroalkyl ketones (in particular, hexafluoroacetone hydrates). Alkaline compound(s) are added in an amount of from about 0.5 to about 5.0 equivalents to the halogen or halogen-containing oxidizing agent, and preferably from about 1.0 to about 2.0 equivalents.

When chlorine or bromine is used as a halogen or a halogen-containing oxidizing agent is used, a buffer solution may also be used instead of water. Examples of preferable buffer solutions include mixtures of salts of organic or inorganic acids, such as citrates, phosphates, succinates, Tris salts (e.g., Tris hydrochloride), borates, acetates, lactates, propionates, etc., together with their respective acids.

Fluoroalkyl ketone hydrates, the target products of the invention, can be purified by conventional processes: for example, the process disclosed in Japanese Unexamined Patent Publication No. 1982-81433, in which calcium chloride or a like salt is added to separate a HFA hydrate; a process in which HFA is extracted using an ethereal solvent such as diisopropyl ether, methyl t-butyl ether or the like, and isolating the hydrate from the organic solvent by distillation; and other processes.

EXAMPLES

Hereinafter, the present invention will be described in more detail with reference to Examples.

Reference Example 1

Preparation of an aqueous potassium 3,3,3-trifluoro-2-trifluoromethyl-2-hydroxypropionate solution In a 500-ml three-necked flask was placed 79.2 g (0.35 mol) of methyl 3,3,3-trifluoro-2-trifluoromethyl-2-hydroxypropionate, and 50 ml of water and 50 ml of methanol were then added. Thereafter, 166 g (0.742 mol, 2.1 eq.) of aqueous 25% KOH solution was slowly added to the mixture while heating and stirring in a hot water bath of 40° C. After 4 hours of the reaction, GC analysis of the reaction liquid confirmed that the starting material ester had disappeared. The reaction liquid was concentrated by an evaporator to distill off methanol and water, giving 154.3 g of aqueous potassium solution.

NMR analysis of this aqueous solution showed that the concentration of potassium 3,3,3-trifluoro-2-trifluoromethyl-2-hydroxypropionate was 56.8% (87.9 g, 0.35 mol).

Reference Example 2

Preparation of an aqueous sodium 3,3,3-trifluoro-2-trifluoromethyl-2-hydroxypropionate solution A 7.63 M NaOH aqueous solution (8.26 ml, 63 mmol) was placed in a 50-ml three-necked flask. 13.6 g (60 mmol) of methyl 3,3,3-trifluoro-2-trifluoromethyl-2-hydroxypropionate was added dropwise at an internal temperature of 40 to 65° C. over 15 minutes. The reaction liquid was then heated at reflux at 73 to 74° C. for 3 hours. GC analysis of the reaction liquid confirmed that the starting material ester had disappeared. NMR analysis of the aqueous solution showed that 60 mmol of sodium 3,3,3-trifluoro-2-trifluoromethyl-2-hydroxypropionate was quantitatively produced.

Examples 1 to 4

Decarboxylation by $F_2$

In a 100-ml four-necked flask were placed water and the aqueous potassium 3,3,3-trifluoro-2-trifluoromethyl-2-hydroxypropionate solution prepared in Reference Example 1. The pH of the mixed solution was 13 due to excess KOH used during hydrolysis. $F_2$ diluted with nitrogen to 5.7 vol % was blown into this solution and reacted under ice-cooling and stirring. A predetermined amount of $F_2$ was passed and the reaction system was purged with nitrogen. Thereafter, the reaction liquid was analyzed.

The results are shown in Table 1.

TABLE 1

| Example | Amount (g) | | $F_2$ flow rate (ml/min) | Reaction time (min) | $F_2$/K salt (eq.) | Conversion (%) | HFA yield (%) |
|---|---|---|---|---|---|---|---|
| | $H_2O$ | K salt solution | | | | | |
| 1 | 26 | 30 | 195 | 90 | 0.65 | 45.5 | 71.9 |
| 2 | 29 | 16 | 195 | 70 | 0.96 | 51.7 | 79.4 |
| 3 | 29 | 16 | 100 | 140 | 0.99 | 45.5 | 88.0 |
| 4 | 29 | 16 | 195 | 100 | 1.37 | 60.3 | 85.3 |

$F_2$: $F_2$ gas diluted with nitrogen to a concentration of 5.7 vol %
Reaction was performed at a temperature of 0 to 5° C.

Example 5

Decarboxylation by $Cl_2$

In a 50-ml three-necked flask were placed 7.85 g (17.8 mmol) of the 56.8% aqueous potassium 3,3,3-trifluoro-2-trifluoromethyl-2-hydroxypropionate solution prepared in Reference Example 1 and 2.46 g (17.8 mmol) of potassium carbonate. 16 g of water was added to dissolve the mixture. The pH was 13. The reaction was performed by blowing chlorine gas at 20 ml/min for 37 minutes (33 mmol, 1.85 eq.) while stirring the solution under heat at 40° C. in a water bath. The pH when the reaction was complete was 6.6. Hexafluoroacetone hydrate was obtained at a starting material conversion of 99.7% with a selectivity of at least 99%.

Example 6

Decarboxylation by $Cl_2$

In a 50-ml three-necked flask were placed 20 mmol of the aqueous sodium 3,3,3-trifluoro-2-trifluoromethyl-2-hydroxypropionate solution prepared in Reference Example 2 and 2.12 g (20 mmol) of sodium carbonate. 20 g of water was added to dissolve the mixture. The pH was 9.8. A reaction was performed by blowing chlorine gas at 20 ml/min for 29 minutes (24.1 mmol, 1.2 eq.) while stirring the solution under heat at 40° C. in a water bath. The pH during this treatment was 6.9. To this solution, 1.06 g (10 mmol) of sodium carbonate was further added, followed by dissolving. The pH was 9.1. The reaction was further performed by blowing chlorine gas at 10 ml/min for 22 minutes (9.2 mmol, 0.46 eq.) while stirring the solution under heat at 40° C. The pH when the reaction was complete was 6.8. Hexafluoroacetone hydrate was obtained at a starting material conversion of 82% with a selectivity of at least 99%.

Example 7

Decarboxylation by Hypochlorite

In a 100-ml three-necked flask was placed 6.52 g (14.8 mmol) of the 56.8% aqueous potassium 3,3,3-trifluoro-2-trifluoromethyl-2-hydroxypropionate solution prepared in Reference Example 1. To this mixture were added 1.7 g of 35% hydrochloric acid and 0.8 g of potassium hydrogencarbonate in this order, thereby adjusting the pH to 8. Subsequently, 24.0 g (32.3 mmol) of 10% aqueous sodium hypochlorite solution was added over one hour while heating the mixture at 40° C. in a water bath, followed by further stirring for 5 hours while maintaining the same temperature. The pH when the reaction was complete was 8. Hexafluoroacetone hydrate was obtained at a starting material conversion of 90% with a selectivity of at least 99%.

Example 8

Decarboxylation by Bromine

In a 50-ml three-necked flask were placed 7.59 g (17.2 mmol) of the aqueous 56.8% potassium 3,3,3-trifluoro-2-trifluoromethyl-2-hydroxypropionate solution prepared in Reference Example 1 and 4.98 g (36 mmol) of potassium carbonate. 25 g of water was added to dissolve the mixture. The pH was 13. 5.75 g (36 mmol) of bromine was added dropwise over 60 minutes while stirring the mixture under heat at 40° C. in a water bath. After the completion of dropwise addition, the reaction was further performed at the same temperature for 3 hours, and the reaction was complete. The pH when the reaction was complete was 7 to 8. Hexafluoroacetone hydrate was obtained at a starting material conversion of 64% with a selectivity of 99% or higher.

Example 9

In a 100-ml PFA bottle was placed 71.7 g of an aqueous solution containing 30.9 g (123.6 mmol) of potassium 3,3,3-trifluoro-2-trifluoromethyl-2-hydroxypropionate and 6 g (80 mmol) of KCl. A direct current of 1 A (8.0 to 8.2 V) was passed through the mixture via platinum electrodes. After 9 hours of electrolysis, NMR analysis of the reaction liquid showed that the conversion and selectivity of the reaction were 90% and at least 99%, respectively. The reaction was performed at room temperature, and the internal temperature of the reaction liquid was 39 to 41° C. The pH when the reaction was complete was 7 to 8.

The invention claimed is:

1. A method for producing a compound represented by formula (2):

$$[CF_3(CF_2)_n][CF_3(CF_2)_m]C(OH)_2 \quad (2)$$

wherein n and m independently represent 0 to 10, the method comprising reacting with a halogen or a halogen-containing oxidizing agent a salt of a compound represented by formula (1):

$$[CF_3(CF_2)_n][CF_3(CF_2)_m]C(OH)COOH \quad (1)$$

wherein n and m independently represent 0 to 10, in the presence of alkaline compound(s).

2. The method according to claim 1, wherein the salt of the compound represented by formula (1) is a salt of 3,3,3-trifluoro-2-trifluoromethyl-2-hydroxypropionic acid.

3. The method according to claim 2, wherein the halogen or halogen-containing oxidizing agent is fluorine diluted with an inert gas.

4. The method according to claim 2, wherein the halogen or halogen-containing oxidizing agent is chlorine.

5. The method according to claim 2, wherein the halogen or halogen-containing oxidizing agent is a hypochlorite or a hypobromite.

6. The method according to claim 5, wherein water is used as a solvent for reacting the salt of the compound of formula (1) with the halogen or halogen-containing oxidizing agent.

7. The method according to claim 6, wherein the salt of the compound of formula (1) is a Li salt, K salt or Na salt.

8. The method according to claim 6, wherein a solvent having a pH of 4 or more is used for reacting the salt of the compound of formula (1) with the halogen or halogen-containing oxidizing agent.

9. The method according to claim 8, wherein chlorine or bromine is produced in the reaction system.

10. The method according to claim 1, wherein the halogen or halogen-containing oxidizing agent is fluorine diluted with an inert gas.

11. The method according to claim 1, wherein the halogen or halogen-containing oxidizing agent is chlorine.

12. The method according to claim 1, wherein the halogen or halogen-containing oxidizing agent is a hypochlorite or a hypobromite.

13. The method according to claim 12, wherein water is used as a solvent for reacting the salt of the compound of formula (1) with the halogen or halogen-containing oxidizing agent.

14. The method according to claim 13, wherein the salt of the compound of formula (1) is a Li salt, K salt or Na salt.

15. The method according to claim 14, wherein a solvent having a pH of 4 or more is used for reacting the salt of the compound of formula (1) with the halogen or halogen-containing oxidizing agent.

16. The method according to claim 1, wherein water is used as a solvent for reacting the salt of the compound of formula (1) with the halogen or halogen-containing oxidizing agent.

17. The method according to claim 2, wherein water is used as a solvent for reacting the salt of the compound of formula (1) with the halogen or halogen-containing oxidizing agent.

18. The method according to claim 3, wherein water is used as a solvent for reacting the salt of the compound of formula (1) with the halogen or halogen-containing oxidizing agent.

19. The method according to claim 4, wherein water is used as a solvent for reacting the salt of the compound of formula (1) with the halogen or halogen-containing oxidizing agent.

20. The method according to claim 10, wherein water is used as a solvent for reacting the salt of the compound of formula (1) with the halogen or halogen-containing oxidizing agent.

21. The method according to claim 11, wherein water is used as a solvent for reacting the salt of the compound of formula (1) with the halogen or halogen-containing oxidizing agent.

22. The method according to claim 12, wherein water is used as a solvent for reacting the salt of the compound of formula (1) with the halogen or halogen-containing oxidizing agent.

23. The method according to claim 1, wherein the salt of the compound of formula (1) is a Li salt, K salt or Na salt.

24. The method according to claim 2, wherein the salt of the compound of formula (1) is a Li salt, K salt or Na salt.

25. The method according to claim 3, wherein the salt of the compound of formula (1) is a Li salt, K salt or Na salt.

26. The method according to claim 4, wherein the salt of the compound of formula (1) is a Li salt, K salt or Na salt.

27. The method according to claim 10, wherein the salt of the compound of formula (1) is a Li salt, K salt or Na salt.

28. The method according to claim 11, wherein the salt of the compound of formula (1) is a Li salt, K salt or Na salt.

29. The method according to claim 12, wherein the salt of the compound of formula (1) is a Li salt, K salt or Na salt.

30. The method according to claim 1, wherein a solvent having a pH of 4 or more is used for reacting the salt of the compound of formula (1) with the halogen or halogen-containing oxidizing agent.

31. The method according to claim 2, wherein a solvent having a pH of 4 or more is used for reacting the salt of the compound of formula (1) with the halogen or halogen-containing oxidizing agent.

32. The method according to claim 3, wherein a solvent having a pH of 4 or more is used for reacting the salt of the compound of formula (1) with the halogen or halogen-containing oxidizing agent.

33. The method according claim 4, wherein a solvent having a pH of 4 or more is used for reacting the salt of the compound of formula (1) with the halogen or halogen-containing oxidizing agent.

34. The method according to claim 1, wherein chlorine or bromine is produced in the reaction system.

35. The method according to claim 2, wherein chlorine or bromine is produced in the reaction system.

36. The method according to claim 3, wherein chlorine or bromine is produced in the reaction system.

37. The method according to claim 4, wherein chlorine or bromine is produced in the reaction system.

38. The method according to claim 10, wherein chlorine or bromine is produced in the reaction system.

39. The method according to claim 11, wherein chlorine or bromine is produced in the reaction system.

40. The method according to claim 12, wherein chlorine or bromine is produced in the reaction system.

* * * * *